US012622433B2

(12) United States Patent
Lakshmi Kanthan et al.

(10) Patent No.: US 12,622,433 B2
(45) Date of Patent: May 12, 2026

(54) BED BUG CONTROL COMPOSITION AND PROCESS OF PREPARING THE SAME

(71) Applicant: COROMANDEL INTERNATIONAL LTD., Secunderabad (IN)

(72) Inventors: Baburaj Lakshmi Kanthan, Chennai (IN); Kothapalli Narasimha Rao, Arlington, TX (US); Sambamoorthy Balaji, Cuddalore (IN); Radhakrishnan Ramamurthi, Cuddalore (IN); Kathiresan Sadhasivam, Cuddalore (IN); Chinaga Suresh Kumar, Cuddalore (IN); Ponnusamy Manimaran, Cuddalore (IN); Govindasamy Jayabal, Cuddalore (IN)

(73) Assignee: COROMANDEL INTERNATIONAL LTD., Secunderabad (IN)

( * ) Notice: Subject to any disclaimer, the term of this patent is extended or adjusted under 35 U.S.C. 154(b) by 984 days.

(21) Appl. No.: 17/621,493

(22) PCT Filed: Jun. 22, 2020

(86) PCT No.: PCT/IB2020/055851
§ 371 (c)(1),
(2) Date: Jan. 18, 2022

(87) PCT Pub. No.: WO2020/261083
PCT Pub. Date: Dec. 30, 2020

(65) Prior Publication Data
US 2022/0346378 A1     Nov. 3, 2022

(30) Foreign Application Priority Data
Jun. 24, 2019   (IN) .............................. 201841048984

(51) Int. Cl.
| *A01N 43/90* | (2006.01) |
| *A01N 37/02* | (2006.01) |
| *A01N 65/22* | (2009.01) |
| *A01N 65/24* | (2009.01) |
| *A01N 65/28* | (2009.01) |
| *A01N 65/44* | (2009.01) |
| *A61K 36/58* | (2006.01) |

(52) U.S. Cl.
CPC ............. *A01N 43/90* (2013.01); *A01N 37/02* (2013.01); *A01N 65/22* (2013.01); *A01N 65/24* (2013.01); *A01N 65/28* (2013.01); *A01N 65/44* (2013.01); *A61K 36/58* (2013.01)

(58) Field of Classification Search
None
See application file for complete search history.

(56) References Cited

U.S. PATENT DOCUMENTS

| 7,179,927 B2 * | 2/2007 | Williams ............. | C07D 519/00 |
| | | | 549/348 |
| 2007/0190094 A1 * | 8/2007 | Bessette ................. | A01N 37/02 |
| | | | 424/770 |

FOREIGN PATENT DOCUMENTS

| WO | WO-2013050967 A1 * | 4/2013 | ............. A01N 25/02 |

OTHER PUBLICATIONS

Elteraifi et al., "Oil and Azadirachtin contents of neem (*Azadirachta indica* A. *Juss*) seed kernels collected from trees growing in different habitats in Sudan", Int. J. Biol. Chem. Sci. 5(3): 1063-1072, Jun. 2011 (Year: 2011).*

* cited by examiner

*Primary Examiner* — Dominic Lazaro
(74) *Attorney, Agent, or Firm* — RMCK Law Group, PLC

(57)     ABSTRACT
The present invention provides a bed bug control composition comprising an azadirachtin extracted from neem seed kernels with a minimum purity 40% but not limited to the same, mixture of plant extracts and additives. The present invention provides a composition comprising azadirachtin, geraniol oil, citronella oil, Cedar wood oil, clove oil, rosemary oil, thyme oil and others. The present invention further provides a process for preparation of bed bug composition.

6 Claims, No Drawings

BED BUG CONTROL COMPOSITION AND PROCESS OF PREPARING THE SAME

CROSS-REFERENCE TO RELATED APPLICATIONS

This application is a 371 U.S. National Stage of International Application No. PCT/IB2020/055851, filed Jun. 22, 2020, which claims priority to Indian Patent Application number 201841048984, filed Jun. 24, 2019. The disclosures of each of the above applications are incorporated herein by reference in their entirety.

FIELD OF THE INVENTION

The present invention relates to a bed bug control formulation. More particularly, the present invention relates to a bed bug control formulation comprising an azadirachtin extracted from neem seed kernels with a minimum purity 40% but not limited to the same, a mixture of plant extracts and additives. The present invention also relates to a process of preparing the bed bug control composition.

BACKGROUND OF THE INVENTION

Bed bugs are members of the genus *Cimex*. *Cimex lectularius* is commonly known bed bug as it prefers to feed on human blood. Other *Cimex* species are specialized to other animals e.g., bat bugs, *Cimex pipistrelli, Cimex pilosellus* and *Cimex adjunctus*. The name of the "bed bug" is derived from the preferred habitat of *Cimex lectularius*: warm houses, especially near or inside of beds, bedding, or other sleep areas.

Bed bugs are tiny insects, ranging from 1-7 mm long and have a flat body shape enabling them to hide in narrow spaces, such as cracks and crevices. The control of bed bug is difficult. Bed bugs have a lifespan ranging from several months to up to four years and are able to go up to a year without a blood meal. Bed bugs are one of the most difficult pest problems to eradicate quickly.

A number of insecticides have been proposed for killing bed bugs. These insecticides are effective in killing bedbugs but their toxicity towards non-targeted living organisms has been a major concern. Potent insecticides such as DDT (dichlorodiphenyltrichloroethane) to weaker insecticides such as pyrethroids have been used to control the bedbug nuisance. Drawbacks of these synthetic insecticides include development of resistance leading to reduced efficacy over time, carcinogenicity to humans and domestic animals, and other detrimental side effects. Also the current eradication strategies for bed bugs are costly, time consuming and often require a professional for implementation.

In the field of insecticides and pesticides, as well as insect and pest repellents, much effort has been given to the development of compositions that are "environment friendly." Accordingly, there has been a great interest in compositions that are readily biodegradable or otherwise compatible with human and animal for use as formulations having little or no toxicity. A limitation associated with developing these types of insecticides or pesticides is that they tend to be less effective and have short residual activity. The pesticides need to be developed with synergistic activity to make them as effective as the toxic chemicals with residual activity.

Botanical insecticides are naturally occurring toxins extracted from plants. They are often less damaging to the environment than conventional synthetic or petroleumbased insecticides. To avoid chemical pesticides, a number of naturally occurring essential oils and their isolates have been evaluated for use as insect repellent. Most botanicals are rapid acting and most but not all botanicals are of low to moderate toxicity to mammals.

Plants are considered as a rich source of bioactive chemicals and they may be an alternative source of bed bug killing agents. Natural products are generally preferred because of their less harmful nature to non-target organisms and due to their innate biodegradability. Existing natural bed bug killing formulations are not so effective.

Azadirachtin is an extract from neem seed kernels of the neem tree. Neem tree is largely grown in India and is used as a commercial insect growth regulator that controls the metamorphosis method as the insect passes from the larva stage to the pupa stage. The Neem tree also yields extracts from its bark, leaves and wood that are used in medicine and cosmetics.

Plant extract is an extract of a compound or multiple compounds from plant/herbs. The structure of plant/herbs is very complex and most of the ingredients are present in the form of organic compounds. However, the present invention shows synergistic effect of plant extracts used to kill bed bugs. The plant extracts includes, but not limited to azadirachtin, geraniol oil, *Eucalyptus* oil, citronella oil, Cedar wood oil, *Eucalyptus* oil, Pepper mint oil, Eugenol, Rosemary oil, Cinnamon oil, Clove oil, Geraniol, Garlic oil, Black pepper oil, Mint oil, Thyme oil, Basil oil, Camphor oil, Lemon grass oil, Henna oil, Cotton seed oil, Cedar leaf oil, Mustard oil, Corn oil, Marigold oil.

Geraniol is a commercially available terpene alcohol that occurs in the essential oils of several aromatic plants. Geraniol is one of the most important molecules in the flavor. In addition to its pleasant odor, geraniol is known to exhibit insecticidal and repellant properties and used as a natural pest control agent exhibiting low toxicity. Geraniol provides protection from mosquitoes, house flies, stable flies, horn flies, cockroaches, fire ants, fleas, gnats, dog ticks, lone star ticks, and no-see-ums.

Citronella oil is a plant extract that is obtained from leaves and stem of one of the plants of the lemongrass specie. When the leaves and stems of this plant are crushed, they release citronella oil. Citronella oil is popularly used as an insect repellent. Citronella is safe and non-toxic to humans and animals.

Clove oil used in dental profession to alleviate pain and as a bacteriostatic and antiseptic is well known. Eugenol, the active ingredient in clove oil also has insect repelling property. Eugenol provides a knock out to pests like mites, ticks and spiders. The pungent odor of clove oil acts directly as a natural insect repellent.

Cedar oil, also known as cedar-wood oil, refers to the volatile whole oil extracts derived principally from the heartwood of *Juniperus virginiana* or *Juniperus ashei*. The cedarwood oil is generally obtained by steam distillation. The crude oil is a viscous liquid having an odor, which is pleasant, sweet woody yet somewhat tar-like or cade-like and smoky. The components found in cedarwood oil include cedrine, cedrol, and thujopsene. Depending on the amount of cedrol in a specific species of cedar can determine its pesticidal effect on insects.

Hence, there is a need in the art to develop an improved composition derived from natural sources that prevent egg hatching and slag (residual) having improved dry residue activity and prolonged activity. There is a need to develop a natural bed bug control composition that is highly effective in killing bed bugs and does not contaminate the atmosphere and human beings with harmful chemicals.

OBJECTS OF THE INVENTION

A primary object of the present invention is to provide novel bed bug control compositions that primarily contain extracts of azadirachtin from neem seed kernels.

In another object of the present invention is to provide bed bug control compositions comprising of an azadirachtin extracted from neem seed kernels with a minimum purity 40% in combination with plant extracts of other plants and additives.

In an another object of the present invention is to provide bed bug control compositions comprising an azadirachtin extracted from neem seed kernels with a minimum purity 40% in combination with plant extracts of Geraniol, Citronella oil, *Eucalyptus* oil, Cedar wood oil, Pepper mint oil, Eugenol, Rosemary oil, Cinnamon oil, Clove oil, Garlic oil, Black pepper oil, Mint oil, Thyme oil, Basil oil, Camphor oil, Lemon grass oil, Henna oil, Cotton seed oil, Cedar leaf oil, Mustard oil, Corn oil, Marigold oil and additives.

In an another object of the present invention is to provide a safe, non-toxic bed bug control composition and methods for killing and/or repelling bed bugs that will not harm the environment.

In an another object of the present invention is to provide a method for controlling bed bugs by the application of effective amounts of a bed bug control composition comprising combinations of azadirachtin with plant extracts of other plants to a locus where such bed bug control is desired.

In an another object of the present invention is to provide a bed bug control composition comprising azadirachtin in combination with plant extracts of other plants that has a pleasant scent and can be applied without burdensome safety precautions.

In another object of the present invention is to provide a process for preparation bed bug control composition.

SUMMARY OF THE INVENTION

The present invention relates to novel bed bug control compositions and process for preparation thereof. The present invention enables, describes, and claims bed bug control compositions comprising azadirachtin, a mixture of plant extracts and additives. Non-limiting examples of plant extracts include from the group consisting of but not limited to Cedar wood oil, *Eucalyptus* oil, Pepper mint oil, Eugenol, Rosemary oil, Cinnamon oil, Clove oil, Citronella oil, Geraniol, Garlic oil, Black pepper oil, Mint oil, Thyme oil, Basil oil, Camphor oil, Lemon grass oil, Henna oil, Cotton seed oil, Cedar leaf oil, Mustard oil, Corn oil, Marigold oil and combinations thereof.

In accordance with another embodiment of the instant invention relates to a bed bug control composition comprising: an azadirachtin extracted from neem seed kernels with a minimum purity 40%, a mixture of any four plant extracts such as Geraniol, Citronella, Clove oil, and Cedar wood oil but not limited to them and can include any other plant extracts, surfactant, solvent and emulsifiers.

In accordance with another embodiment of the instant invention relates to a bed bug control composition comprising an azadirachtin present in an amount in range from 0.1% to 80.0% (w/w), a mixture of any four plant extracts but not limited to of Geraniol, Citronella oil, Clove oil, Cedar wood oil, *Eucalyptus* oil, Pepper mint oil, Eugenol, Rosemary oil, Cinnamon oil, Clove oil, Citronella oil, Geraniol, Garlic oil, Black pepper oil, Mint oil, Thyme oil, Basil oil, Camphor oil, Lemon grass oil, Henna oil, Cotton seed oil, Cedar leaf oil, Mustard oil, Corn oil, Marigold oil present in a range from 1.0% to 90.0% (w/w), surfactant in a range from 1.0% to 90% (w/w), solvent present in an amount in range from 1.0% to 80.0% (w/w), and emulsifiers present in an amount range from 2.0% to 80.0% (w/w).

In accordance with another embodiment of the instant invention provides a process for preparation of bed bug composition comprising steps of: weighing azadirachtin extracted from neem seed kernels with a minimum purity 40% but not limited to the same in a predetermined amount, weighing solvent in predetermined amount, adding solvent to azadirachtin with continuous stirring at 250 rpm for 30 minutes, adding mixture of plant extracts in a predetermined amount, adding surfactant and emulsifier with continuous stirring for 60 minutes.

In accordance with another embodiment of the instant invention relates to the method of applying the bed bug control composition by spraying, fogging or treating with aerosol.

DESCRIPTION OF THE INVENTION

The present invention provides a novel, stable and bio-efficacious bed bug control composition. The novel composition of the present invention comprises combination of azadirachtin and plant extracts but not limited to Geraniol, Citronella oil, Cedar wood oil, Clove oil along with other additives.

It is to be noted, as used in the specification and claims, the singular forms "a", "an", and "the" include plural referents unless the context clearly dictates otherwise. Thus, for example, reference to a composition containing "a compound includes a mixture of two or more compounds. It should also be noted that the term "or" is generally employed in its sense including "and/or" unless the content clearly dictates otherwise. The expression of various quantities in the terms of "% w/w" or "%" means the percentage by weight, relative to the weight of the total composition unless otherwise specified.

The phrase "controlling bedbug" as used in the present invention includes killing of the bed bug or its offspring; killing of larval stages of the bed bug, killing of the bed bug's eggs, starving the bed bug, suffocating the bed bug, reducing the number of the bed bugs present at the target site, preventing settlement of the bed bug at the target site, rendering the bed bug inactive, or knockdown of the bed bug.

As used herein, "knockdown" activity refers to the pesticidal activity of a composition as applied directly to a bed bug.

As used herein, the term "effective amount" regarding a composition to control pest refers to that dosage of active substance sufficient to exert the desired activity.

A pest is an animal that is detrimental to humans or human affairs, or that annoys a person. Pests include all insects and spiders. The term "pest" includes organisms belonging to Arthropods, in particular *Chelicerata, Tracheata*, but not *Crustacea*. In the present invention the target pest is *Cimex lectularius* or *Cimex hemipterus* for which the composition is formulated.

As used herein, "surface" or "target surface" includes a surface to which a bed bug control composition is applied or is to be applied. Such surfaces may include, for example, a surface where bed bugs are likely to contact or otherwise be exposed to the applied bed bug control composition, to lay their eggs, and/or a surface that has been or is suspected to be infested by bed bugs.

As used herein, the term "stability" means the ability of a composition to retain its bed bug killing activity after application to a surface to be treated with bed bug control composition.

Neem (*Azadirachta indica*), is a tropical evergreen tree. Neem oil is derived from the fruits and seeds of a neem tree. Methods for obtaining neem oil, azadirachtin extract or other derivatives purified from neem oil are known in the art. One exemplary method for obtaining neem oil is cold pressing. The most important active constituent in neem oil is azadirachtin and the others are nimbolinin, nimbin, nimbidin, nimbidol, sodium nimbinate, gedunin, salannin, and quercetin. Azadirachtin is a chemical compound belonging to the limonoid group. The azadirachtin is a secondary metabolite present in the Neem seeds. The azadirachtin is a highly oxidized tetranortriterpenoid which boasts a plethora of oxygen functionality, comprising an enol ether, acetal, hemiacetal and tetra-substituted oxirane as well as a variety of carboxylic esters. The azadirachtin in the present invention is obtained from the seed kernels of the Neem Tree (*Azadirachta indica*).

An azadirachtin extracted from neem seed kernels have purity in a range of 1% to 97%, preferably a minimum purity 40%. Azadirachtin extract contributes to multiple possible modes of action, such as repellent, insect killer. Azadirachtin with the help of suitable surfactants and solvents can penetrate the cuticle of the bed bug, translocate in its body and kill the bed bug. Azadirachtin is regarded as nontoxic to mammals, to the environment, and UV or heat promotes its degradation. Neem oil and its derivatives for e.g. Azadirachtin contributes to controlling pests including insects, mites, ticks, and nematodes also by affecting the pest's behavior and physiology. In contrast, neem products are non-toxic to higher animals and most beneficial insects. The range of azadirachtin in the present invention is 0.1% to 80.0% (w/w) of the bed bug killing composition.

Plant extracts are volatile oils and natural products. Plant extracts have been known for centuries in many cases and even millennia, and this term is well known in the art. Plant extracts are available commercially. A plant extract carries a distinctive odor, scent, or essence, of the plant; therefore, plant extracts convey characteristic fragrances. A botanical source is odorous if an odor can be detected by any animal, or pest not just a human; "odorous" thus is simply an indication that some volatile component is present in the plant. Because of their hydrophobic nature, plant extracts are not readily miscible in water. In the present invention the plant extracts may be any plant extracts but not limited to Cedar wood oil, Clove oil, Citronella oil, Geraniol, *Eucalyptus* oil, Pepper mint oil, Eugenol, Rosemary oil, Cinnamon oil, Garlic oil, Black pepper oil, Mint oil, Thyme oil, Basil oil, Camphor oil, Lemon grass oil, Henna oil, Cotton seed oil, Cedar leaf oil, Mustard oil, Corn oil, Marigold oil or any combination thereof. Preferably, the plant extract used in the present invention are geraniol oil, citronella oil, clove oil, cedar wood oil, rosemary oil, thyme oil, and others. The plant extract in the present invention provides synergistic effect with the main active ingredient azadirachtin in the composition. The range of the plant extracts is between 1% to 90% (w/w) of the bed bug killing composition.

In an embodiment of the present invention, a plant extract is a predominately volatile material or materials isolated by some physical (as opposed to chemical) process from an odorous, single-species, botanical source. The oils extracted by the physical process can contain some non-volatile material. A most widely used process for the isolation of plant extract is steam distillation of plant matter, although dry distillation, supercritical fluid extraction, and solvent extraction are also used.

The term "solvent" as used herein refers to an aromatic or aliphatic solvent, with which an active ingredient can be mixed or formulated to facilitate its application, storage, transport, and/or handling, or improve various product characteristics such as its odor. Commonly used solvent include, but are not limited to, Tert-Amyl alcohol, Benzyl alcohol, 1,4-Butanediol, 1,2,4-Butanetriol, Butanol, 2-Butanol, N-Butanol, Tert-Butyl alcohol, Di(propylene glycol) methyl ether, Diethylene glycol, Ethanol, Ethylene glycol, 2-Ethylhexanol, Furfuryl alcohol, Glycerol, Isobutanol, Isopropyl alcohol, Methanol, 2-(2-Methoxyethoxy)ethanol, 2-Methyl-1-butanol, 2-Methyl-1-pentanol, 3-Methyl-2-butanol, Neopentyl alcohol, 2-Pentanol, 1,3-Propanediol, 1-Propanol, Propylene glycol, Propylene glycol methyl ether, Benzyl benzoate, Bis(2-ethylhexyl) adipate, Bis(2-ethylhexyl) phthalate, 2-Butoxyethanol acetate, Butyl acetate, Sec-Butyl acetate, Tert-Butyl acetate, Diethyl carbonate, Dimethyl adipate, Dioctyl terephthalate, Ethyl acetate, Ethyl acetoacetate, Ethyl butyrate, Ethyl lactate, Ethylene carbonate, Hexyl acetate, Isoamyl acetate, Isobutyl acetate, Isopropyl acetate, Methyl acetate, Methyl lactate, Methyl phenylacetate, Methyl propionate, Propyl acetate, Propylene carbonate, Triacetin, methyl acetate, tert-butyl acetate, dimethyl carbonate, propylene carbonate, propylene glycol monomethyl ether, propylene glycol monopropyl ether, dipropylene glycol monopropyl ether, propylene glycol monobutyl ether, dipropylene glycol monobutyl ether, propylene glycol, dipropylene glycol, propylene carbonate, ethylene glycol monomethyl ether, diethylene glycol monomethyl ether, ethylene glycol monobutyl ether, diethylene glycol monobutyl ether, cyclohexane, cycloheptane, methyl cyclohexane, 1,4-dimethyl cyclohexane, benzene, amyl benzene, secondary butyl benzene, toluene, o-ethyl toluene, o-xylene, 4-ethyl-o-xylene, m-xylene, p-xylene, 2-ethyl-p-xylene. Butyl acetate is an organic compound with a molecular formula of $C_6H_{12}O_2$ which occurs naturally in food products. It is a colorless liquid with a low viscosity, having a sweet banana-like odor. This liquid is volatile but flammable in nature. Ethyl acetate is an effective poison for use in insect collector as its vapours are a respiratory tract irritant whose vapours can kill the insect quickly without destroying it. Preferably, the solvent used is butyl acetate and ethyl acetate. The range of the solvent is between 1% to 90% (w/w) of the bed bug killing composition.

The term "surfactant" as used herein refers to compounds which rupture the insect cuticle and allows active ingredient in the composition to penetrate & translocate within insect body leading to death of bed bugs. The surfactants used herein include, but are not limited to Tween-85, Tween-20, Tween-80, Polyethylene glycol, Tween-60, Polysorbate, Span-80, Span-60, Trilaurin, Triolein, Span 20, Sorbitan trioleate, Isopropyl myristate, poly acrylate, ethoxylated alcohols, ethoxylated fatty esters, alkoxylated glycols, ethoxylated fatty acids, carboxylated alcohols, carboxylic acids, fatty acids, ethoxylated alkylphenols, fatty esters, sodium dodecylsulfide, other fatty acid-based surfactants, other natural or synthetic surfactants, or a combination thereof and combinations thereof. Preferably the surfactant used is ethoxylated castor oil or Tween 85. The surfactant is used in the range of 1 to 90% (w/w) of the bed bug killing composition.

The term "emulsifier" as used herein refers to compounds that stabilizes the composition of the present invention. The emulsifiers used herein include, but are not limited to silicone based emulsifiers, non-silicone based emulsifier, Olive oil, Cashew oil, Castor oil, Sunflower oil, Pongamia oil, Sesame oil, Linseed oil, Rice Bran oil, Ground nut oil and other oils of plant and animal origin and combinations thereof. The oils can be in any of their chemical forms. Preferably the emulsifier used is silicone oil. The emulsifier is used in the range of 2% to 80% (w/w) of the bed bug killing composition.

The composition of the present invention can be used as ready to use (RTU) and also can be used as emulsified concentrate (EC) formulation by dissolving in required quantity of water and sprayed on desired location. The formulation can also be used in an aerosol form. The formulation is prepared as emulsifiable concentrate or aerosol by using processes known in state of the art.

A method for controlling bed bugs, or bed bugs infestation insects in a target area comprise the step of identifying a target area suspected of having bed bugs, followed by treating the target area by applying an effective amount of bed bug control composition effective to control or kill the bed bugs, to the target area, and monitoring the effectiveness of the treatment by said methods at a regular or pre-determined time interval.

Application of the composition of the present invention results in death of bed bugs with low to no toxic effect to humans, animals, or environment. One benefit of the present application is a cost-effective alternative to synthetic chemicals, heat, cold, tenting, etc. When the composition is applied so that direct contact with the bed bug occurs, the bed bug cannot survive; such contact kill composition provides fast relief.

The following examples illustrate, but in no way are intended to limit the present invention.

Example 1: Process for Formulating Different Formulations

The primary active ingredient azadirachtin extracted from neem seed kernels with a minimum purity 40% but not limited to the same is weighed in predetermined amount as given in Table 1 and is taken in a vessel. The pre-determined amount of solvent is added slowly with a continuous stirring at 250 rpm for 30 min. To this solution other plant extracts like geraniol oil, clove oil, citronella oil, cedar wood oil, thyme oil, rosemary oil and others are added in the ranges as given in Table 1 with constant stirring at 250 rpm for 30 min. Further, surfactant and emulsifier is added to the reaction mixture with continued stirring for another 60 min to obtain a final formulation. The mixing is carried out at ambient temperature and pressure. Various examples of combinations of different plant extracts in combination with azadirachtin and other additives for the control of Bed bugs are provided in Table 1.

TABLE 1

| | | | | | | | | | |
|---|---|---|---|---|---|---|---|---|---|
| Different formulations of bed bug control composition | | | | | | | | | |
| Formulation | Azadirachtin (40% Purity) (% w/w) | Geraniol (% w/w) | Citronellla Oil (% w/w) | Cedar wood oil (% w/w) | Clove Oil (% w/w) | Emulsifier (% w/w) | Surfactant (% w/w) | Solvent (% w/w) | |
| 1 | 0.1 | 1 | 1 | 1 | 1 | 2 | 1[#] | 92.9* | |
| 2 | 80 | 1 | 1 | 1 | 1 | 2 | 1[#] | 13* | |
| 3 | 80 | 2 | 1 | 1 | 1 | 2 | 1[#] | 12* | |
| 4 | 0.33 | 90 | 1 | 1 | 1 | 2 | 1[#] | 3.67** | |
| 5 | 0.33 | 1 | 1 | 1 | 1 | 80 | 1[#] | 14.67* | |
| 6 | 0.33 | 1 | 1 | 1 | 1 | 1 | 90[#] | 4.67** | |
| 7 | 0.33 | 1 | 3 | 2 | 1 | 1 | 1[##] | 90.67** | |

*Butyl acetate;
**Ethyl acetate
[#]Ethoxylated Castor oil;
[##]Tween 85

| Formulation | Azadirachtin (40% Purity) (% w/w) | Geraniol (% w/w) | Citronellla Oil (% w/w) | Plant Extract (% w/w) | Paraffin oil (carrier) | Emulsifier (% w/w) | Surfactant (% w/w) | Solvent (% w/w) |
|---|---|---|---|---|---|---|---|---|
| 8 | 0.33 | 8 | 2 | 5[$] | 2 | 5 | 6[#] | 71.67* |
| 9 | 0.33 | 8 | 2 | 5[$] | 2 | 5 | 5[#] | 72.67* |
| 11 | 0.33 | 8 | 2 | 5[$$] | 3 | 5 | 3[#] | 73.67* |

*Butyl acetate
[#]Castrox100
[$]Eugenol;
[$$]Clove oil

| Formulation | Azadirachtin (40% Purity) (% w/w) | Geraniol (% w/w) | Peppermint Oil (% w/w) | Eugenol (% w/w) | Paraffin oil (carrier) | Emulsifier (% w/w) | Surfactant (% w/w) | Solvent (% w/w) |
|---|---|---|---|---|---|---|---|---|
| 12 | 0.33 | 8 | 2 | 5 | 3 | 5 | 0 | 76.67* |

*Butyl acetate

| | Azadirachtin (40% Purity) | Geraniol | Citronella Oil | Clove Oil | Plant Extract | Paraffin Oil | Emulsifier | Surfactant | Solvent |
|---|---|---|---|---|---|---|---|---|---|

TABLE 1-continued

| Different formulations of bed bug control composition | | | | | | | | |
|---|---|---|---|---|---|---|---|---|
| Formulation | (% w/w) | (% w/w) | (% w/w) | (% w/w) | (% w/w) | (% w/w) | (% w/w) | (% w/w) |
| 10 | 0.33 | 8 | 2 | 3$ | 2@ | 0 | 7 | 3# | 74.67* |
| 13 | 0.33 | 8 | 2 | 3$$ | 2@@ | 3 | 7 | 3# | 71.67* |
| 14 | 0.33 | 8 | 2 | 3$$ | 2@@@ | 0 | 7 | 3# | 74.67* |

@Rosemary oil;
@@Thyme oil;
@@@Cedar wood oil
Castrox-100
*Butyl acetate
$Eugenol;
$$Clove oil

Example 2: Shelf Life of Bed Bug Killing Formulations

The formulations from example 1 were analysed for stability through accelerated stability study at 54° C. and 50% RH. The result of the stability study is tabulated in Table 2. The stability study is known as accelerated stability study as it is not done in real time but conducted at 54° C. and 50% RH. The prepared formulations are transferred into glass vials and placed inside a stability chamber to analyse the degradation of the active material. Generally for azadirachtin, 7 days of accelerated stability study is equivalent to 6 months in real time stability.

TABLE 2

| Shelf life stability of the bed bug control formulations | | | |
|---|---|---|---|
| | | | Accelerated stability details |
| S. No. | Formulation details | Shelf life achieved | % of Azadirachtin degradation @35th day |
| 1 | Formulation 8 | 2 years | 9.17 |
| 2 | Formulation 9 | 2 years | 8.80 |
| 3 | Formulation 10 | 2 years | 8.76 |
| 4 | Formulation 11 | 2 years | 8.90 |
| 5 | Formulation 12 | 2 years | 8.97 |
| 6 | Formulation 13 | 2 years | 9.21 |
| 7 | Formulation 14 | 2 years | 9.07 |

It was observed that all the formulations were stable for a shelf life period of 1 year to 2 years.

Example 3: Method for Determining the Synergy of the Bed Bug Control Composition The indicative bio-efficacy studies were carried out as per CIB&RC norms (Central insecticides Board and Registration Committee). In the experiment bed bug control formulations are sprayed in different doses to different test surfaces like wood, glass, cement, tiles and mud using Potter tower. After spraying the different test surfaces are kept for air drying for 24 hour prior to screening test. Adult bed bugs of randomly mixed sex and age were transferred from rearing jars into test surfaces for the study. In the present study 10 adult bed bugs were transferred on to the test surfaces. Experiment was conducted in triplicate and cumulative knock down was counted at every 5 minutes intervals up to 30 minutes. Then the bed bugs were collected and placed in a recovery jar, observed for 24 hours mortality and results were expressed in percentage of mortality. In control, the test surfaces are sprayed with distilled water. The indicative bio-efficacy study is carried out on the 14 bed bug control formulations as prepared in example 1. The formulations were applied at 1 ml/sq. ft. dose on two different surfaces such as Tiles and Glass.

TABLE 3

| Bed bug bio-efficacy results for developed formulation Bio-efficacy results of Bed bug control formulation | | | |
|---|---|---|---|
| | | Mortality % | |
| Formulation description | Dose (ml/sq ft) | Tiles | Glass |
| Formulation 1 | 1 | 12 | 15 |
| Formulation 2 | 1 | 20 | 32 |
| Formulation 3 | 1 | 14 | 16 |
| Formulation 4 | 1 | 30 | 15 |
| Formulation 5 | 1 | 19 | 22 |
| Formulation 6 | 1 | 15 | 35 |
| Formulation 7 | 1 | 17 | 19 |
| Formulation 8 | 1 | 18 | 33 |
| Formulation 9 | 1 | 27 | 20 |
| Formulation 10 | 1 | 23 | 20 |
| Formulation 11 | 1 | 33 | 30 |
| Formulation 12 | 1 | 23 | 13 |
| Formulation 13 | 1 | 27 | 20 |
| Formulation 14 | 1 | 37 | 30 |

Based on the indicative bio-efficacy data in Table 3, the two best formulations (Formulation 8 and 14) were shortlisted for further bio-efficacy test. The Formulation 8 and 14 were tested at four different doses of 8, 10, 14 and 16 ml/sq. ft. on five different surfaces such as Tiles, Glass, Wood, Cement and Mud. The same procedure as described above was repeated for determining the bio-efficacy of the two compositions. It was observed that Formulation 14 is more effective than Formulation 8, at 8 ml/sq. ft. and 10 ml/sq. ft. dose produced 100% mortality on Tiles and Glass surfaces and 86.6% mortality on wood surface, Formulation 14 was also effective on cement and mud surfaces at 10 ml/sq. ft. dose respectively. Doses at 14 and 16 ml/sq. ft. of Formulation 14 on mud surface produced 70% and 90% mortality respectively. The bio-efficacy data of the two formulations is given in Table 4.

TABLE 4

| Formulation description | Dose (ml/sq. ft.) | Mortality % on various surfaces | | | | |
|---|---|---|---|---|---|---|
| | | Tiles | Glass | Wood | Cement | Mud |
| Formulation 8 | 8 | 96.67 | 100 | 10 | 0 | 0 |
| | 10 | 100 | 100 | 10 | 0 | 0 |
| | 14 | | | | | 60 |
| | 16 | | | | | 86.67 |
| Formulation 14 | 8 | 100 | 100 | 23.33 | 13.33 | 0 |
| | 10 | 100 | 100 | 86.67 | 73.33 | 43.33 |
| | 14 | | | | | 70 |
| | 16 | | | 90 | 80 | 90 |

Bed bug bio-efficacy results for developed formulation
Bio-efficacy results of Bed bug control formulation Example 4: Method of Using the Bed Bug Control Formulation A person desirous of getting a target surface rid of bed bugs may spray the composition of the present invention on different target surfaces where bedbugs can be found such as wood, fabric made of any material, curtain, floors, bed, cement tiles etc. Alternatively, the person can also apply the composition by using a cotton material soaked with the formulation, which is then used to wipe any surface to have activity against bedbugs. The composition can also be applied by fogging at the target area. The person may inspect the target area for signs of hatched pests 5 to 10 days after applying the bed bug control composition; and reapplying the bed bug control composition if signs of hatched bed bugs are observed.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A bed bug control composition comprising:
an azadirachtin extract of a minimum percentage purity of 40% present in a range from 0.1% 80% (w/w);

a mixture of plant extracts selected from the group consisting of:
geraniol present in a range from 1% to 90% (w/w),
citronella oil present in a range from 1% to 3% (w/w),
clove oil present in a range from 1% to 5% (w/w),
cedar wood oil present in a range from 1% to 2% (w/w),
rosemary oil present in a range from 1% to 2% (w/w),
thyme oil present in a range from 1% to 2% (w/w),
eugenol present in a range from 1% to 5% (w/w), and
peppermint oil in a range from 1% to 2% (w/w); and
additives present in a range from 0.1% to 90% (w/w),
wherein the additives consist of one or more solvents, one or more surfactants, and one or more emulsifiers,
wherein the one or more solvents are selected from butyl acetate, ethyl acetate, or a combination thereof.

2. The bed bug control composition as claimed in claim 1, wherein the one or more surfactants are selected from the group consisting of ethoxylated alcohols, ethoxylated fatty esters, alkoxylated glycols, ethoxylated fatty acids, carboxylated alcohols, carboxylic acids, fatty acids, ethoxylated alkylphenols, fatty esters, sodium dodecylsulfide, fatty acid-based surfactants, natural surfactants, synthetic surfactants, and a combination thereof.

3. The bed bug control composition as claimed in claim 1, wherein the one or more emulsifiers are selected from silicone based emulsifiers, non-silicone based emulsifier, Olive oil, Cashew oil, Castor oil, Sunflower oil, Pongamia oil, Sesame oil, Linseed oil, Rice Bran oil, Ground nut oil, plant oils, animal oils, and combinations thereof.

4. The bed bug control composition as claimed in claim 1, wherein the composition is formulated in a form of a Ready to Use (RTU) or an Emulsified concentrate (EC).

5. A process for preparation of the bed bug control composition of claim 1, comprising the steps of:
weighing the azadirachtin extracted from neem seed kernels in a predetermined amount,
weighing the one or more solvents in a predetermined amount,
adding the one or more solvents to the azadirachtin extracted from neem seed kernels with continuous stirring at 250 rpm for 30 minutes,
adding the mixture of plant extracts in a predetermined amount,
adding the one or more surfactants and the one or more emulsifiers with continuous stirring for 60 minutes.

6. The process as claimed in claim 5, wherein stirring is carried out at ambient temperature and pressure.

* * * * *